United States Patent
Lindner et al.

(10) Patent No.: US 7,679,519 B2
(45) Date of Patent: Mar. 16, 2010

(54) APPARATUS FOR IMPROVED PULSE OXIMETRY MEASUREMENT

(75) Inventors: Bernd Lindner, Ratekau (DE); Martin Eckermann, Rostock (DE); Thomas Scholl, Wismar (DE); Steven Gorski, Eagle, WI (US)

(73) Assignee: Envitec-Wismar GmbH (DE)

( * ) Notice: Subject to any disclaimer, the term of this patent is extended or adjusted under 35 U.S.C. 154(b) by 687 days.

(21) Appl. No.: 11/269,524

(22) Filed: Nov. 7, 2005

(65) Prior Publication Data
US 2006/0129039 A1    Jun. 15, 2006

Related U.S. Application Data (60) Provisional application No. 60/522,772, filed on Nov. 5, 2004.

(51) Int. Cl.
*G08B 23/00* (2006.01)
(52) U.S. Cl. .................... 340/573.1; 340/540; 600/483; 600/511; 600/513
(58) Field of Classification Search .............. 340/573.1, 340/506, 540, 693.5; 600/483, 511, 513, 600/549
See application file for complete search history.

(56) References Cited

U.S. PATENT DOCUMENTS

| | | | |
|---|---|---|---|
| 4,685,464 A | 8/1987 | Goldberger et al. | |
| 4,938,218 A * | 7/1990 | Goodman et al. | 600/338 |
| 5,513,642 A * | 5/1996 | Ostrander | 600/334 |
| 5,817,008 A | 10/1998 | Rafert et al. | |
| 6,519,487 B1 | 2/2003 | Parker | |
| 7,096,054 B2 * | 8/2006 | Abdul-Hafiz et al. | 600/344 |

FOREIGN PATENT DOCUMENTS

| | | |
|---|---|---|
| WO | WO 01/13790 A1 | 3/2001 |
| WO | WO 2006/104790 A1 | 10/2006 |

OTHER PUBLICATIONS

PCT International Preliminary Report on Patentability of International Application No. PCT/IB2005/004122.
PCT Search Report of International Application No. PCT/IB2005/004122.

* cited by examiner

*Primary Examiner*—Daryl Pope
(74) *Attorney, Agent, or Firm*—Factor & Lake (57) ABSTRACT

An apparatus for measuring the blood oxygen level of a patient is disclosed. In one embodiment, the apparatus includes a housing having an interior surface of non-reflective material substantially surrounding an interior. A cooperating light source and detector are operatively positioned proximate the interior surface so as to emit and receive light projected within the interior of the housing. A material more conducive to light transmission, reflectance, or a combination thereof—as compared to the interior surface material—is positioned proximate the light source and/or detector.

37 Claims, 7 Drawing Sheets

FIG. 9 Comparison of R-3512-9 (old type of build) and R-3512-20 (white inset, old pad)

| sensor | amperage [μA] | | | |
| --- | --- | --- | --- | --- |
| | probe off | | finger | |
| | Red | Ired | Red | Ired |
| R-3512-20 | 66.45 | 75.56 | 1.01 | 0.71 |
| R-3512-9 | 35.90 | 35.58 | 0.44 | 0.34 |
| percent difference | 185.11 30.55 | 212.38 39.98 | 229.55 0.57 | 208.82 0.37 |

| sensor | transmittance [μA/mA] | | | |
| --- | --- | --- | --- | --- |
| | probe off | | finger | |
| | Red | Ired | Red | Ired |
| R-3512-20 | 3322.5 | 3778.0 | 50.5 | 35.5 |
| R-3512-9 | 1794.9 | 1778.9 | 22.0 | 17.0 |
| percent difference | 185.1 1527.63 | 212.4 1999.13 | 229.5 28.50 | 208.8 18.50 |

FIG. 10 Comparison of R-3512-9 (old type of build) and R-3512-20 (white inset, new pad)

| sensor | amperage [μA] | | | |
|---|---|---|---|---|
| | probe off | | finger | |
| | Red | Ired | Red | Ired |
| R-3512-20 | 62.15 | 74.41 | 1.54 | 1.34 |
| R-3512-9 | 35.90 | 35.58 | 0.44 | 0.34 |
| percent | 173.13 | 209.15 | 350.00 | 394.12 |
| difference | 26.25 | 38.83 | 1.10 | 1.00 |

| sensor | transmittance [μA/mA] | | | |
|---|---|---|---|---|
| | probe off | | finger | |
| | Red | Ired | Red | Ired |
| R-3512-20 | 3107.5 | 3720.5 | 77.0 | 67.0 |
| R-3512-9 | 1794.9 | 1778.9 | 22.0 | 17.0 |
| percent | 173.1 | 209.1 | 350.0 | 394.1 |
| difference | 1312.63 | 1941.63 | 55.00 | 50.00 |

FIG. 11 Comparison of R-3512-20 (old type of build with white insert) and (white inset, new pad)

| sensor | amperage [μA] | | | |
|---|---|---|---|---|
| | probe off | | finger | |
| | Red | Ired | Red | Ired |
| R-3512-20 old housing | 66.45 | 75.56 | 1.01 | 0.71 |
| R-3512-20 new housing | 62.15 | 74.41 | 1.54 | 1.34 |
| percent | 93.53 | 98.48 | 152.48 | 188.73 |
| difference | 4.30 | 1.15 | -0.53 | -0.63 |

FIG. 12 Comparison of R-3512-9 (old type of build) and R-3512-40 (white inset, new pad)

| sensor | amperage [μA] | | | |
|---|---|---|---|---|
| | probe off | | finger | |
| | Red | Ired | Red | Ired |
| R-3512-9 | 37.06 | 39.08 | 0.71 | 0.70 |
| R-3512-40 | 64.62 | 74.64 | 2.28 | 2.54 |
| percent | 174.39 | 191.02 | 323.40 | 362.86 |
| difference | 27.57 | 35.57 | 1.58 | 1.84 |

| sensor | transmittance [μA/mA] | | | |
|---|---|---|---|---|
| | probe off | | finger | |
| | Red | Ired | Red | Ired |
| R-3512-9 | 1852.8 | 1953.8 | 35.3 | 35.0 |
| R-3512-40 | 3231.0 | 3732.0 | 114.0 | 127.0 |
| difference | 1378.25 | 1778.25 | 78.75 | 92.00 |

APPARATUS FOR IMPROVED PULSE OXIMETRY MEASUREMENT

RELATED APPLICATIONS

This application claims the benefit of U.S. Provisional Patent Application Ser. No. 60/522,772, filed Nov. 5, 2004; the contents of which are incorporated herein by reference.

FIELD OF THE INVENTION

The present invention relates generally to the measurement of arterial oxygen saturation by non-invasive electro-optical sensing—commonly referred to in practice as pulse oximetry—and more specifically to an apparatus for optimizing electro-optical signals utilized in the measurement.

BACKGROUND OF THE INVENTION

Pulse oximetry utilizes an electro-optical sensor attached to a patient and a monitor that measures the electro-optical signals and calculates patient oxygenation. Because of its simplicity, reliability, and ability to quickly report changes in patient oxygenation status, pulse oximetry measurement has been employed for the past twenty years as a standard of care in critical care monitoring of patients.

External or non-invasive pulse oximetry devices typically utilize light transmittance or reflectance technology incorporating a light source and a detector (or sensor) operatively attached to an individual. Light emitted from the light source is passed through the individual's tissue wherein a portion thereof is received by the sensor and analyzed to determine the blood saturation level of the tissue.

Nearly all pulse oximeter devices employ two LED light sources (red and infrared) and a silicon photodiode for the measurement in the sensor. Various sensor topologies have been utilized in the prior art, including finger type "clip" sensors, disposable sensors constructed in tape laminates, elastomer based tube sensors, and multi-site "Y" or "flag" shaped sensors. All these sensors use the above electro-optical elements in combination with cable and connector configurations that allow connection to the appropriate monitor type.

In practice, LED light sources are sequentially pulsed and the light enters a patient site that contains an arterial bed, e.g., finger or toe. After passing through the site, a portion of the light is received by a photodetector and converted into a current that may be on the order of several to tens of microamperes in magnitude. This relatively small electrical signal is transmitted via a sensor cable (and an extension cable, if necessary) to a monitor, where it is amplified, measured, and interpreted according to the monitor's measurement algorithm(s).

Because oximetry generally relies upon detection and measurement of minute current signals, effects related to signal-to-noise limitations should be considered. The operational environment for oximeter devices typically includes other electronic devices nearby, e.g., surgical equipment. Some common techniques used to address signal-to-noise performance include utilization of shielded cables and detectors, and a method of pulsing of the LED's at a high current (on the order of 40 to 400 mA) for a short duty cycle to temporarily boost the light output and detector signal. However, such techniques necessarily will not overcome all the signal-to-noise limitations inherent in the measurement of minute currents. Additionally, LED intensity levels may gradually decline over the life of the sensor and may lead to an eventual failure of providing usable signal levels.

A typical reusable finger clip SpO2 sensor is comprised of a hinged housing made of rigid plastic, which holds flexible pads that contact a patient's skin, e.g., finger. The pads contain optical elements preferably covered with a transparent material, e.g., layer, pane, window; that facilitate measurements through the patient's finger. One particular finger clip sensor, the Nellcor DS-100A, has pads made from a white silicone material, and a clip configuration that is open and permits ambient light to enter the finger from the sides. Ambient light is therefore added to the detector baseline signal, and may in some cases affect the signal measurement quality.

Figure 2:
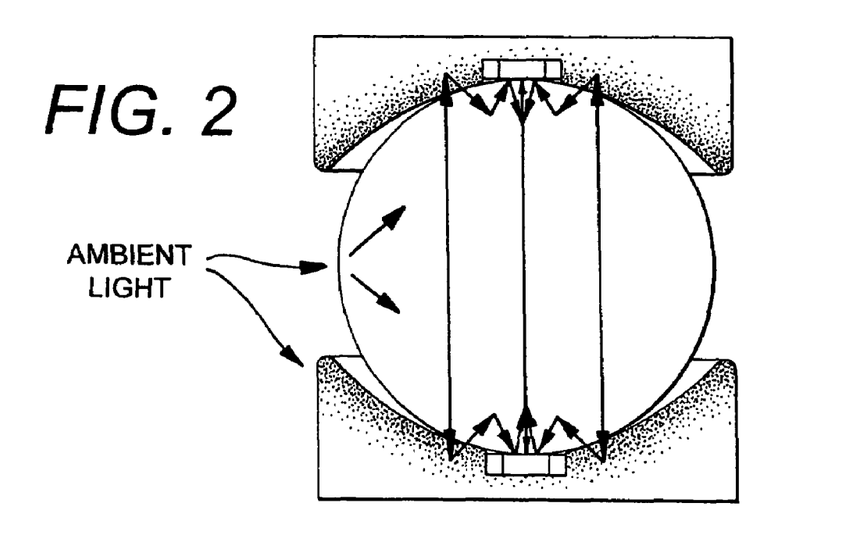
FIG. 2 is cross-sectional view of a commonly known sensor geometry depicting multiple transmitted, reflected, and scattered paths of light.

The white color of the pads is generally highly reflective in both the red and infrared wavelengths present in the sensor, and assists the reflectance of several internal pathways. As such, utilization of the white pads facilitates the throughput of the generated light signals and generally provides a more efficient transfer of light from the LED to the detector. Referring to FIG. 2, the diagram is illustrative of this feature—showing light exiting the light source and passing through the finger via multiple transmissive, reflective, and scattering paths and entering the detector.

While the complexity of the finger and white pad as reflective and scattering media makes exact characterization of the light paths difficult, it can be readily demonstrated that a white pad facilitates more throughput of measurable light than the equivalent optics in a darker pad. As can also be seen, ambient light may also reach the detector by travelling through the finger or reaching the pad. Therefore the white pad is efficient in light transmission, but remains susceptible to ambient light interference.

Another sensor, the BCI 3044 Finger Clip sensor, utilizes a rigid housing that extends over the pads to reduce the influence of ambient light, as well as finger-contacting gray colored pads. Another sensor, the HP M1191A, utilizes a sensor housing constructed primarily of a gray rubber tube that surrounds the finger. Although both of these sensors have the advantage of reducing the admittance of far less ambient light, throughput efficiency of the light signals is reduced due to the darker pad.

Dark pads (and coverings) reduce susceptibility to ambient light, but are less desirable for directing the light from the transmitters (LED's) to the receiver (photodiode) because of less efficient utilization of internal reflectances. In practice, dark pads are less desirable because signal detector current levels may be reduced by a factor of 2-3 as compared to light colored pads.

In summary, utilization of the sensors described above requires an unfavourable trade-off between signal quantity and susceptibility to ambient light interference. That is, optimal detection and measurement parameters are not provided by use of either monocolor light (white) or dark (gray, black) pads.

The present invention is intended to address these as well as other shortcomings in the prior art.

SUMMARY OF THE INVENTION

The present invention generally provides a sensor device for non-invasively measuring a blood oxygen level of a patient. In an embodiment, the sensor device comprises a bi-color pad topology that includes a material having a reflectance and/or transmittance characteristic to light, e.g., light color, that is proximate to a light emitting device, e.g., OPTO device; and another material over the rest of the pad or housing—in the case of a tube-like sensor device—having a relatively less reflectance and/or transmittance characteristic to that of the light color material. This novel configuration simultaneously addresses concerns involving increased light level reception and reduced susceptibility to ambient light and is especially useful in the construction of rubber tube type sensor devices.

In a further aspect of the present invention, the sensor comprises a housing including an interior surface substantially surrounding an interior and including a first material that is substantially non-reflective and/or non-transmissive to light. A light source is affixed to the housing and proximate the interior surface so as to project light within the interior of the housing. A light detector is affixed to the housing and proximate the interior surface. A second material is proximate the light source or the light detector, wherein the second material includes a property that is relatively more reflective, transmissive, or a combination thereof, to light than the first material.

According to another aspect of the present invention, a sensor utilized in monitoring patient oxygenation comprises a housing including a material that is substantially non-reflective and/or non-transmissive to light. The housing includes an interior and an interior surface having an opening. An inset housing includes a material that is more reflective and/or transmissive than the housing material and is inlaid within the opening of the interior surface. A light source is substantially surrounded by the inset housing wherein an exposed portion of the light source is proximate the interior surface so as to project light within the interior of the housing.

According to a further aspect of the present invention, a sensor capable of attachment to a patient for monitoring oxygenation comprises a housing having an interior wall substantially surrounding an interior. The interior wall includes a non-reflective material and an outlet, and is capable of being placed proximate the patient's skin. An inset housing includes a reflective and/or transmissive material and is inlaid within the outlet. A light source is substantially surrounded by the inset housing wherein an exposed portion of the light source is positioned proximate the interior wall so as to project light produced by the light source toward the interior of the housing. A light detector for receiving illuminations of the light source—preferably red or infrared—is operatively attached to the housing and proximate the interior.

In a still further aspect of the present invention, a portion of the interior wall is continuous; and may also include a segment that is coplanar with an interior plane. Additionally, a segment of the non-reflective material and a segment of the reflective and/or transmissive material are coplanar with the interior plane.

In yet another aspect of the present invention, a transparent material, e.g., layer, pane, window; is positioned between the light source and the interior, and/or between the light detector and the interior.

These and other aspects of the present invention will be apparent after consideration of the written description, drawings, and claims herein.

BRIEF DESCRIPTION OF THE DRAWINGS

The invention will now be described with reference to the drawings wherein.

DETAILED DESCRIPTION OF THE PRESENT INVENTION

While this invention is susceptible of embodiment in many different forms, there is shown in the drawings and will herein be described in detail one or more embodiments with the understanding that the present disclosure is to be considered as an exemplification of the principles of the present invention and is not intended to be limited to the embodiments illustrated.

It is to be understood that like or analogous elements and/or components referred to herein may be identified throughout the drawings with like reference characters.

Figure 1:
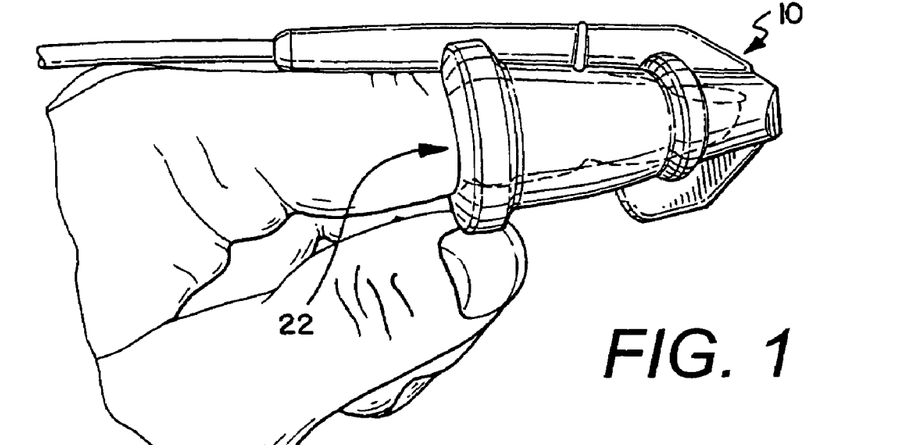
FIG. 1 is perspective drawings of one embodiment of the present invention.

One embodiment of the present invention is shown in FIG. 1 as a sensor device 10 utilized in monitoring patient oxygenation. Referring to FIGS. 3-8, several configurations of the sensor 10 are shown to include a housing 12 including an interior surface 24 that may be continuous in at least one direction. The interior surface 24 substantially surrounds an interior 22 and includes a first material that is substantially non-reflective and/or non-transmissive to light. A light source 14 is operatively affixed to the housing 12 and proximate the interior surface 24 so as to project light within the interior 22 of the housing. A light detector is 20 operatively affixed to the housing 12 and proximate the interior surface 24. And a second material is proximate the light source 14 or the light detector 20, wherein the second material is relatively more reflective, transmissive—or a combination thereof—to light as compared to the first material of the interior surface 24. The light source 14 or detector 20 can be operatively attached to the interior surface 24 wherein the reflective and/or transmissive material is positioned about the light source or detector. In a preferred embodiment, the material substantially surrounding the light source 14 and/or detector 20 is reflective primarily in the red (approximately 660 nm) and infrared (approximately 880-940 nm) regions.

Figure 3:
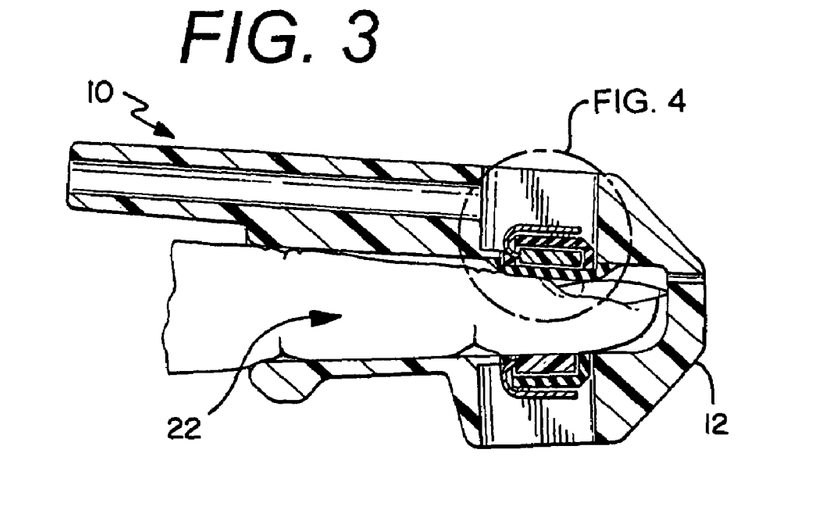
FIG. 3 is cross-sectional view of a tube type sensor according to one embodiment of the present invention.
Figure 4:
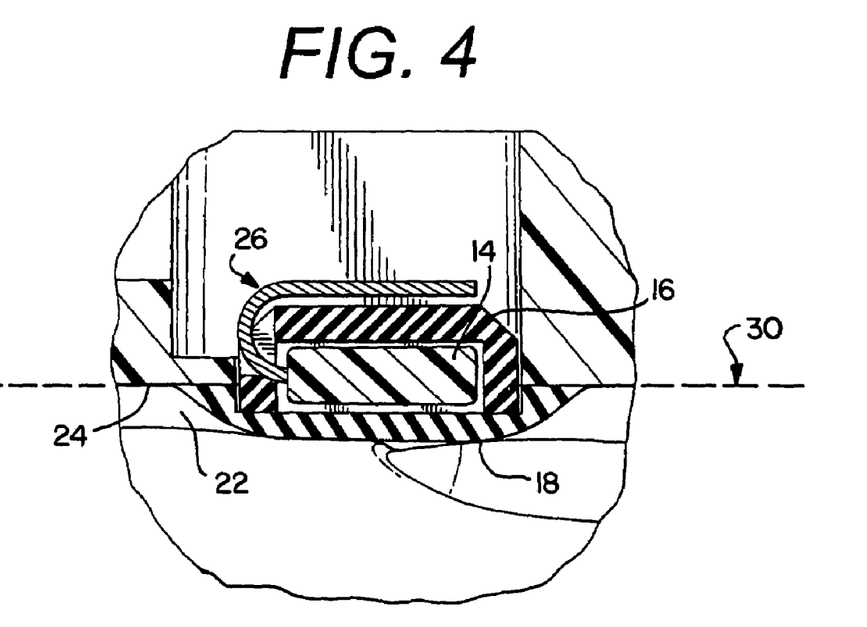
FIG. 4 is a magnified view of a portion of the tube type sensor shown in FIG. 3.
Figure 5:
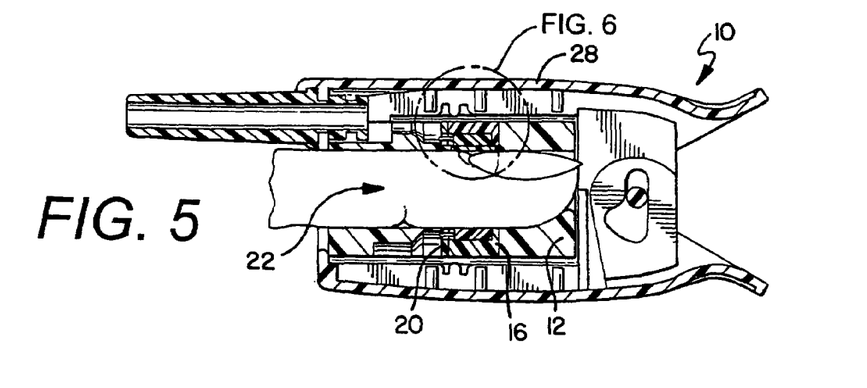
FIG. 5 is cross-sectional view of a clip type sensor according to one embodiment of the present invention.

The present invention shown in FIGS. 3 and 4 is in the form of a soft-tip tube-type sensor surrounding a finger tip wherein the housing 12 is constructed of a flexible, substantially non-reflective and/or transmissive material☐preferably dark colored rubber☐and includes an interior 22 wherein a patient's tissue, e.g., phalanges, can be placed. An interior surface 24 or wall substantially surrounds the interior 22 and includes an opening 26 or outlet. The sensor 10 shown in FIGS. 5 and 6 includes a shell 28 in the form of a relatively less flexible material, e.g., plastic, that operatively encases the housing 12.

The sensor 10 preferably includes a light source 14—red and/or infrared light—substantially surrounded by an inset housing 16. The inset housing 16 includes a material that is relatively more reflective and/or transmissive to light, e.g., white silicone rubber, than that of the interior surface 24 and is inlaid within the opening 26 or outlet of the interior surface. An exposed portion of the light source 14 is proximate the interior surface 24 so as to project light toward the interior 22 of the housing 12.

The inset housing 16 is substantially surrounded by the housing 12 and its non-reflective material that preferably extends at least one millimeter about the perimeter of the light source 14. The white colored material of the inset housing 16 facilitates internal reflections of light near this region as well as the overall light transmission throughput; while at the same time, the darker colored—relatively less reflective and/or transmissive—material of the housing 12 blocks admittance of ambient light.

Additionally, a transparent material 18, e.g., layer or pane, may be positioned proximate the light source 14 to more effectively couple the light near the patient's tissue. Referring to FIG. 4, a layer of transparent material 18 covers the embedded light source 14 and inset housing 16. In this configuration, a portion of the inset housing 16 and/or the light source 14 intersects a plane 30 coplanar with a portion of the interior surface 24 and protrudes into the interior 22 of the housing 12. The transparent material 18 preferably covers at least a portion of the interior surface 24, the light source 14, and the reflective inset housing 16.

Figure 6:
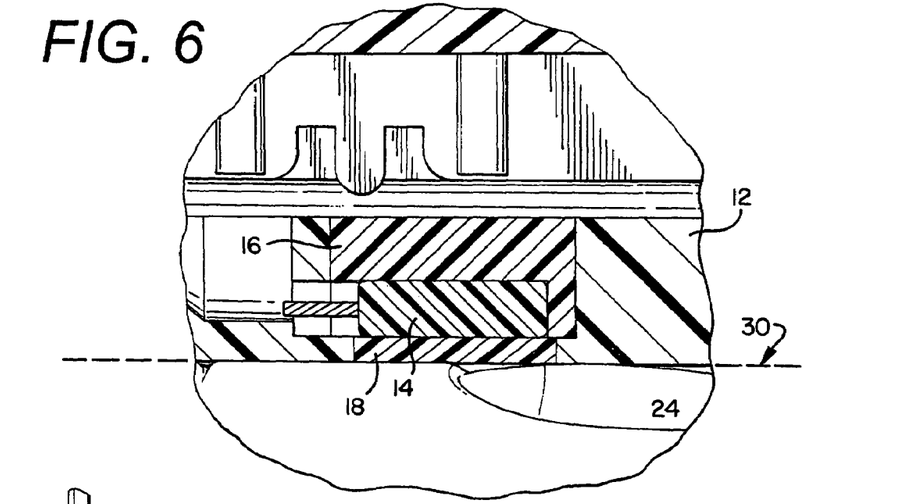
FIG. 6 is a magnified view of a portion of the clip type sensor shown in FIG. 5.
Figures 7, 8:
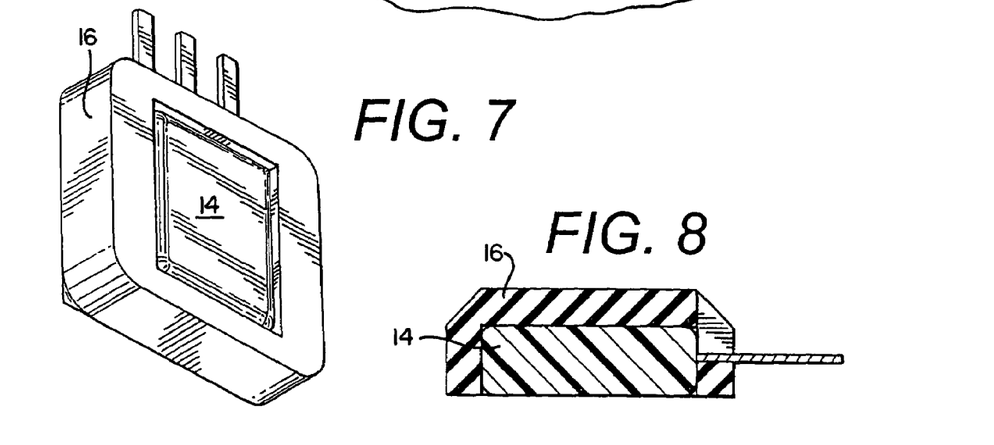
FIG. 7 is a perspective view one embodiment of the light source and inset housing of the present invention.
FIG. 8 is a cross-section view of FIG. 7.
Figure 9:
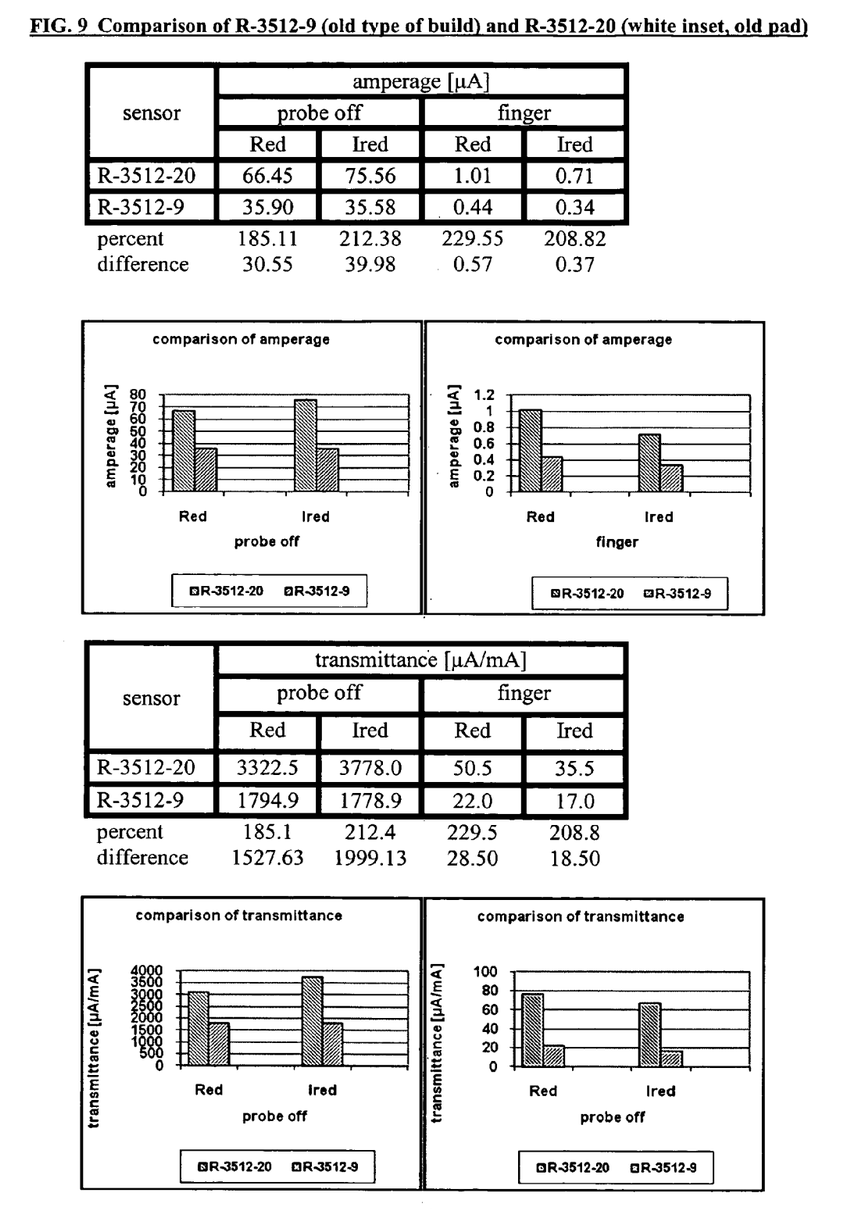
FIG. 9 is a comparison of amperage and transmittance of components R-3512-9 (old type of build) and R-3512-20 (white inset, old pad) in table and chart form.
Figure 10:
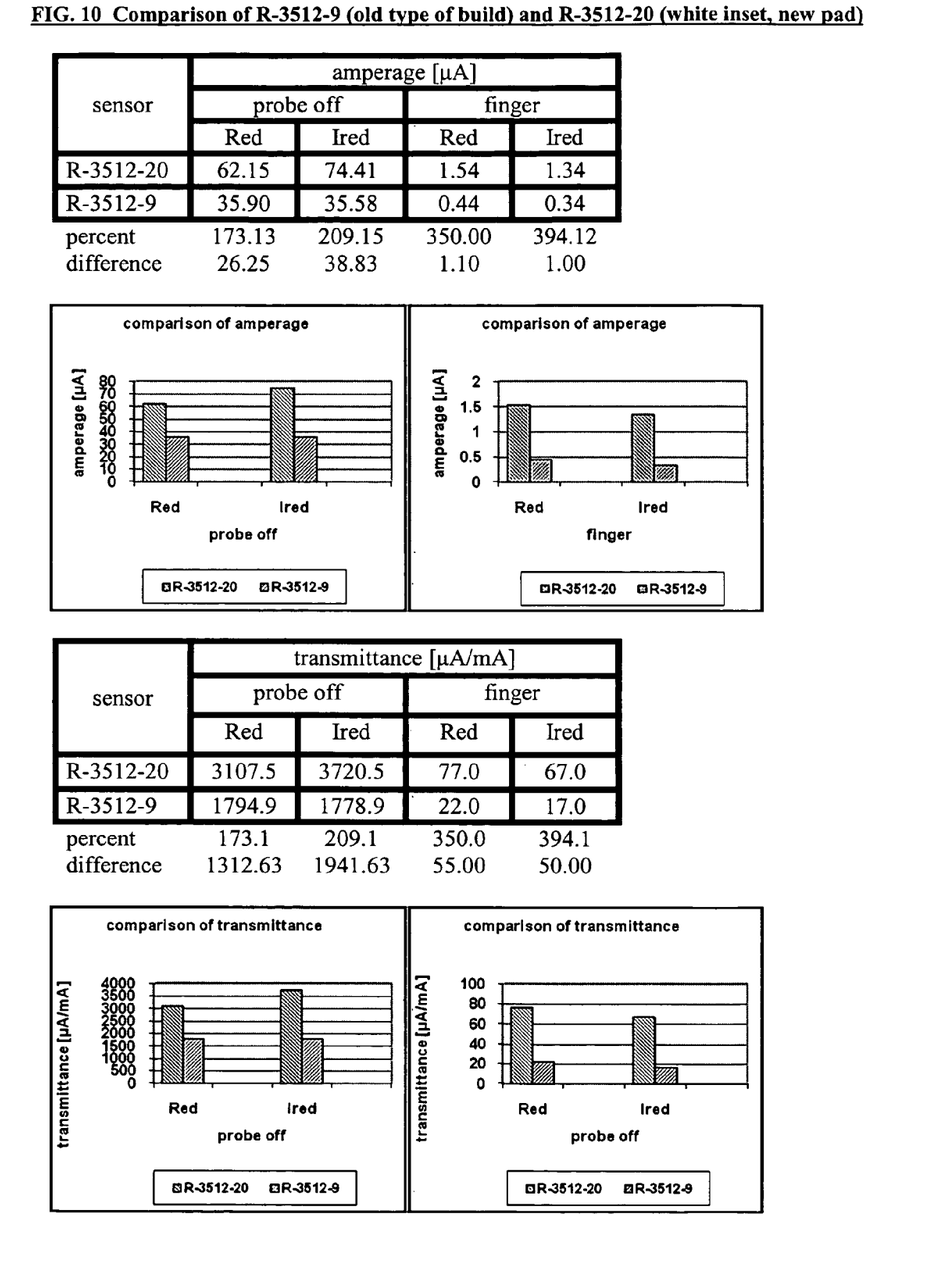
FIG. 10 is a comparison of amperage and transmittance of components R-3512-9 (old type of build) and R-3512-20 (white inset, new pad); in table and chart form.
Figure 11:
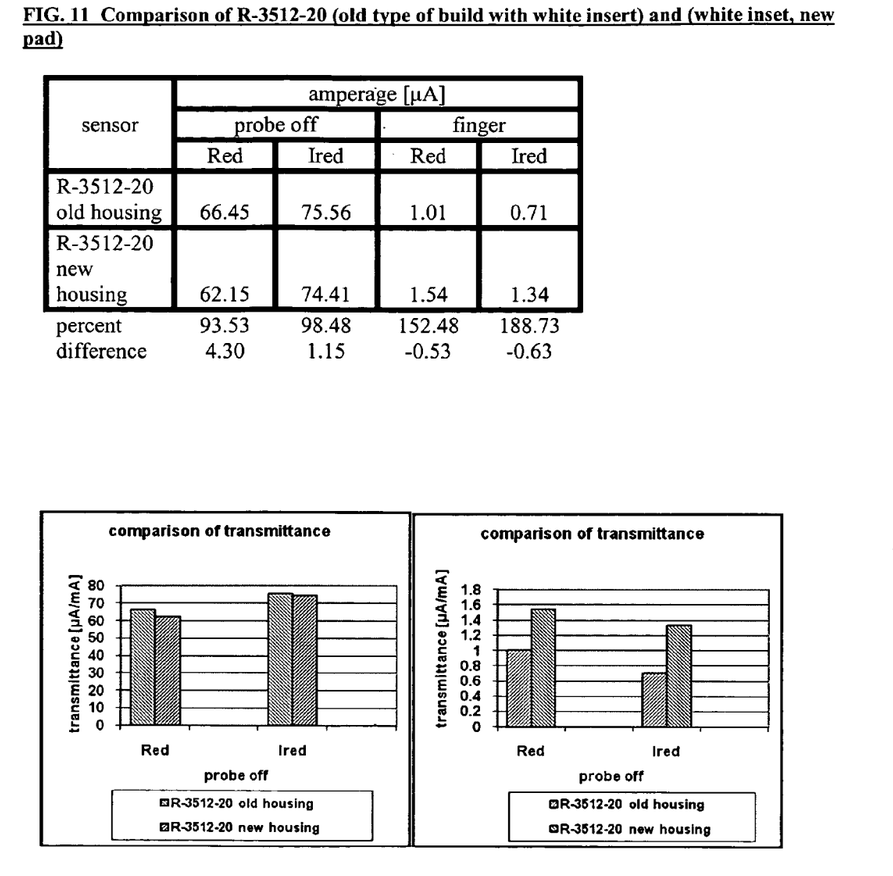
FIG. 11 is a comparison of amperage of components R-3512-20 (old type of build with white inset) and (white inset, new pad) in table form; and, a comparison of transmittance of components R-3512-20 (old type of build with white inset) and (white inset, new pad) in chart form; and, FIG. 12 is a comparison of amperage and transmittance of components R-3512-9 (old type of build) and R-3512-40 (white inset, new pad); in table and chart form.
Figure 12:
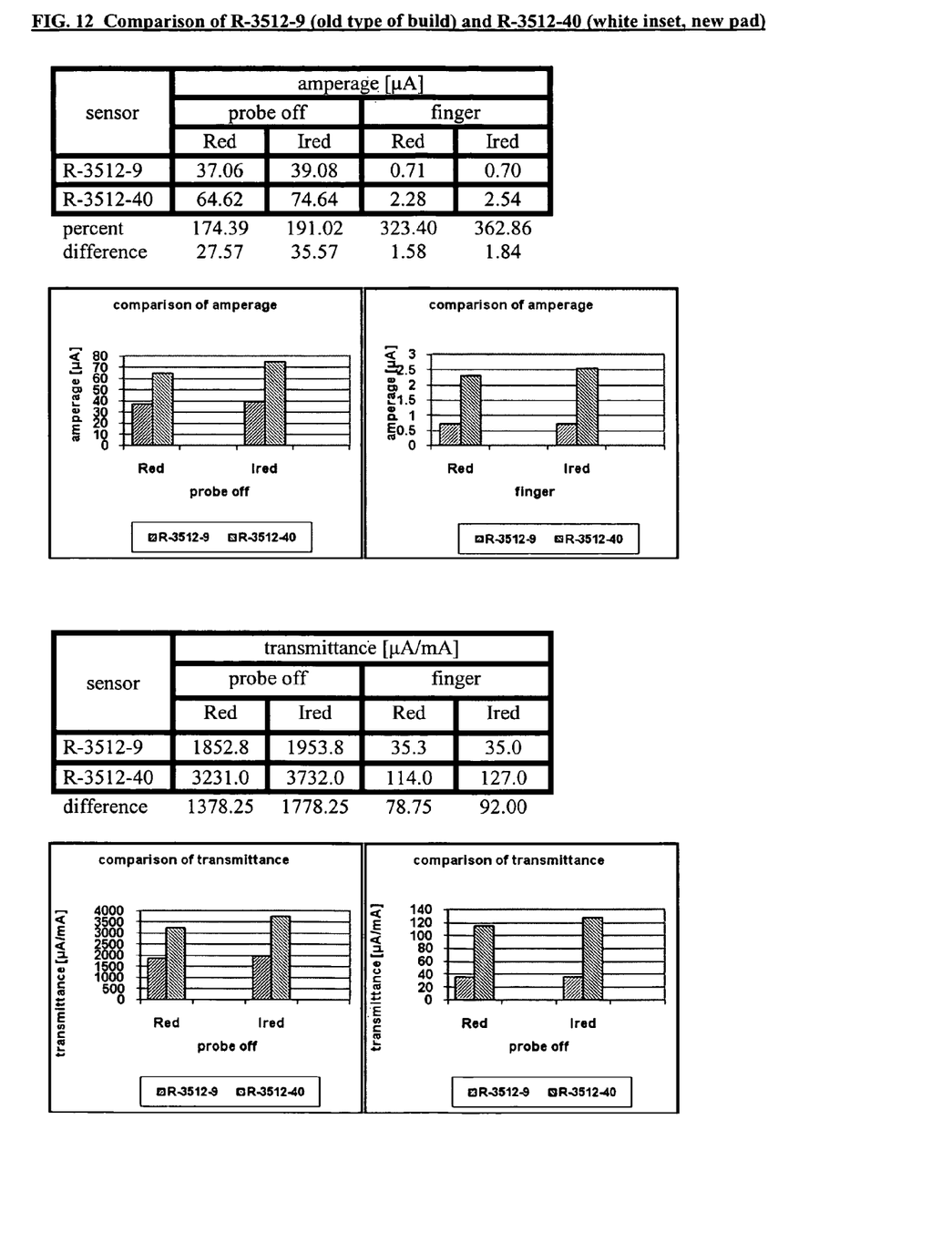

In FIG. 6, the pane of transparent material 18 is proximate the light source 14 and the inset housing 16, and flush—coplanar—with the interior wall 24. As such, the plane 30 adjacent the patient's tissue includes a portion of the non-reflective material of the interior surface 24 and the transparent material 18.

The light detector 20 can be configured within an inset housing 16 having a reflective and/or transparent material inlaid within the non-reflective interior surface 24 similar to that proximate the light source 14.

For either type of sensor 10 configuration disclosed above, i.e., flexible tube or clip pad, the white colored region of the inset housing 16 may be completely surrounded by darker colored material of the housing 12 and/or interior surface 24 as provided by common insert molding techniques and other methods that allow the molded housing or pad to fully enclose the more reflective and/or transmissive material from the rear.

In a further embodiment of the present invention, portions of the light source 14 and the detector 20 substantially lie within the same plane. In a still further embodiment, a portion of the plane 30 is curvilinear to facilitate placement of the sensor—and that of its light source 14 and/or detector 20—adjacent the patient's tissue, e.g., finger, toe. It is to be understood that one of ordinary skill in the art would appreciate that the present invention is capable of various configurations—with respect to the housing 12, inset housing 16, light source 14, transparent material 18, plane 30, interior surface 24, and/or the interior 22—are responsive to particular applications, e.g., reflective technology, and are considered to be within its scope.

Comparative measurements of light throughput can be used to assess relative light efficiency. These measurements, sometimes called trans-conductance tests, assess the detector output current at specified DC levels of LED illumination. To test a sensor, LED's are illuminated one at a time at a fixed current such as 20 mA DC, and the detector current is recorded for each LED (red and infrared). This may be performed with an empty sensor ("probe off finger" condition), a test subject's finger, or a finger model such as a plastic rod. Perhaps the most meaningful comparative test of light throughput uses a test subject's finger, with the condition that the same finger be used within a short period of time in a similar position on all sensors to be compared.

The following comparison of transmittance includes three sensors A1, A2, and B. Sensor A1 includes the sensor having a close fit to the finger and the white inset housing of the present invention. Sensor A2 includes the white inset housing of the present invention in a sensor that does not have as close a fit to the finger as A1. Sensor B includes neither the close fit of A1 nor the white inset of the present invention.

Chart 1 below details comparative light efficiency results for the rubber type sensors A1, A2, and B. Transmittance readings provide similar information normalized for LED current as µA(detector output)/mA(LED current).

CHART 1

| | Transmittance Comparison. | | | | | | | |
|---|---|---|---|---|---|---|---|---|
| | AMPERAGE (µA) | | | | TRANSMITTANCE (µA/mA) | | | |
| | PROBE OFF | | FINGER | | PROBE OFF | | FINGER | |
| SENSOR | RED | IRED | RED | IRED | RED | IRED | RED | IRED |
| A1 (white inset and close finger fit) | 62.15 | 47.14 | 1.54 | 1.34 | 3107.5 | 3720.5 | 77.0 | 67.0 |
| A2 (white inset) | 66.45 | 75.56 | 1.01 | 0.71 | 3322.5 | 3778.0 | 50.5 | 35.5 |
| B | 30.20 | 28.88 | 0.30 | 0.21 | 1510.0 | 1444.0 | 15.0 | 10.5 |
| | 36.13 | 36.73 | 0.49 | 0.39 | 1806.5 | 1836.5 | 24.5 | 19.5 |
| | 42.11 | 39.74 | 0.42 | 0.31 | 2105.5 | 1987.0 | 21.0 | 15.5 |
| | 35.15 | 36.96 | 0.55 | 0.45 | 1757.5 | 1848.0 | 27.5 | 22.5 |

With reference to Chart 1, comparison of the difference in transmittance between sensor A1 configured with the sensor fitted closely to the finger and the white inset of the present invention; sensor A2 configured with the white inset of the present invention; and sensor B configured with neither the close fit of A1 nor the white inset of the present invention, can readily be shown. Referring to the "finger" columns (utilizing a subject test finger), it can be seen that for sensor B utilizing only a gray rubber housing overall, the average red light transmittance was 22 units and the average infrared light transmittance was 17 units. Incorporation of the white inset housing of the present invention in sensor A2 increased red and infrared light intensity levels to 50.5 and 35.5, respectively—representing a nominal doubling of light efficiency. When configuring the sensor to include the white inset housing of the present invention and the closer fitting to the finger (sensor A1), the light efficiency improved to more than three times that of sensor B.

Chart 1 illustrates that utilization of the white inset in the sensor—located in the region of the optical devices—an substantially improve sensor light efficiency while simultaneously rejecting ambient light. Although the sensor is but one component of an oximeter monitoring system, signal-to-noise improvements in the sensor may be translated into performance improvements in the system. For example, compromised perfusion, i.e., poor arterial blood circulation, at a measurement site represents one of the significant challenges to SpO2 monitors, and a modest improvement in signal-to-noise may mean the difference between function and non-function under extreme conditions.

The charts and graphs shown in FIGS. 9-12 compare the amperage and/or transmittance of the known sensor and the sensors embodying the present invention that were compiled and shown above in Chart 1. Namely, EnviteC's R-3512 series rubber tube type sensors wherein sensor R-3512-9 is a known type of build, not as closely fit to the finger (referred to in Chart 1 as sensor B); sensor R-3512-20 includes the reflective white inset housing of the present invention and closely fit to the finger (referred to in Chart 1 as sensor A1); and sensor R-3512-20 includes the known type of build and the reflective white inset housing of the present invention (referred to in Chart 1 as sensor A2).

Comparison of R-3512-9 (Old Type of Build) and R-3512-20 (White Inset, Old Pad)

| | amperage [μA] | | | |
| | probe off | | finger | |
| sensor | Red | Ired | Red | Ired |
| --- | --- | --- | --- | --- |
| R-3512-20 | 66.45 | 75.56 | 1.01 | 0.71 |
| R-3512-9 | 35.90 | 35.58 | 0.44 | 0.34 |
| percent | 185.11 | 212.38 | 229.55 | 208.82 |
| difference | 30.55 | 39.98 | 0.57 | 0.37 |

| | transmittance [μA/mA] | | | |
| | probe off | | finger | |
| sensor | Red | Ired | Red | Ired |
| --- | --- | --- | --- | --- |
| R-3512-20 | 3322.5 | 3778.0 | 50.5 | 35.5 |
| R-3512-9 | 1794.9 | 1778.9 | 22.0 | 17.0 |
| percent | 185.1 | 212.4 | 229.5 | 208.8 |
| difference | 1527.63 | 1999.13 | 28.50 | 18.50 |

Comparison of R-3512-9 (Old Type of Build) and R-3512-20 (White Inset, New Pad)

| | amperage [μA] | | | |
| | probe off | | finger | |
| sensor | Red | Ired | Red | Ired |
| --- | --- | --- | --- | --- |
| R-3512-20 | 62.15 | 74.41 | 1.54 | 1.34 |
| R-3512-9 | 35.90 | 35.58 | 0.44 | 0.34 |
| percent | 173.13 | 209.15 | 350.00 | 394.12 |
| difference | 26.25 | 38.83 | 1.10 | 1.00 |

| | transmittance [μA/mA] | | | |
| | probe off | | finger | |
| sensor | Red | Ired | Red | Ired |
| --- | --- | --- | --- | --- |
| R-3512-20 | 3107.5 | 3720.5 | 77.0 | 67.0 |
| R-3512-9 | 1794.9 | 1778.9 | 22.0 | 17.0 |
| percent | 173.1 | 209.1 | 350.0 | 394.1 |
| difference | 1312.63 | 1941.63 | 55.00 | 50.00 |

Comparison of R-3512-20 (Old Type of Build with White Insert) and (White Inset New Pad)

| | amperage [μA] | | | |
| | probe off | | finger | |
| sensor | Red | Ired | Red | Ired |
| --- | --- | --- | --- | --- |
| R-3512-20 old housing | 66.45 | 75.56 | 1.01 | 0.71 |
| R-3512-20 new housing | 62.15 | 74.41 | 1.54 | 1.34 |
| percent | 93.53 | 98.48 | 152.48 | 188.73 |
| difference | 4.30 | 1.15 | −0.53 | −0.63 |

Comparison of R-3512-9 (Old Type of Build) and R-3512-40 (White Inset, New Pad)

| | amperage [μA] | | | |
| | probe off | | finger | |
| sensor | Red | Ired | Red | Ired |
| --- | --- | --- | --- | --- |
| R-3512-9 | 37.06 | 39.08 | 0.71 | 0.70 |
| R-3512-40 | 64.62 | 74.64 | 2.28 | 2.54 |
| percent | 174.39 | 191.02 | 323.40 | 362.86 |
| difference | 27.57 | 35.57 | 1.58 | 1.84 |

| | transmittance [μA/mA] | | | |
|---|---|---|---|---|
| | probe off | | finger | |
| sensor | Red | Ired | Red | Ired |
| R-3512-9 | 1852.8 | 1953.8 | 35.3 | 35.0 |
| R-3512-40 | 3231.0 | 3732.0 | 114.0 | 127.0 |
| difference | 1378.25 | 1778.25 | 78.75 | 92.00 |

While specific embodiments have been illustrated and described, numerous modifications may come to mind without significantly departing from the spirit of the invention, and the scope of protection is only limited by the scope of the accompanying Claims.

What is claimed is:

1. A sensor utilized in monitoring patient oxygenation, the sensor comprising:
a housing including an interior surface substantially surrounding an interior and including a first material having a low reflectance and/or transmissive characteristic to light;
a light source operatively affixed to the housing and proximate the interior surface so as to project light within the interior of the housing;
a light detector operatively affixed to the housing and proximate the interior surface; and,
a second material proximate the light source or the light detector, wherein the second material being relatively more reflective, transmissive—or a combination thereof—to light than the first material.

2. The sensor of claim 1 wherein a portion of the interior surface is continuous.

3. The sensor of claim 1 wherein a portion of the light source extends into the interior of the housing.

4. The sensor of claim 1 further comprising:
a transparent material positioned proximate the light source.

5. The sensor of claim 4 wherein the transparent material being positioned between the light source and the interior of the housing.

6. The sensor of claim 4 wherein the transparent material is a pane substantially coplanar with a portion of the interior surface.

7. The sensor of claim 1 wherein the first material comprises a dark color.

8. The sensor of claim 7 wherein the dark color is black or gray.

9. The sensor of claim 1 wherein the second material comprises a light color.

10. The sensor of claim 9 wherein the light color is white.

11. The sensor of claim 1 wherein the light source illuminates red wavelength.

12. The sensor of claim 1 wherein the light source illuminates infrared wavelength.

13. The sensor of claim 1 wherein the housing comprises a flexible material.

14. The sensor of claim 1 wherein a portion of the interior surface is coplanar with an interior plane, and a portion of the first material and a portion of the second material are coplanar with the interior plane.

15. The sensor of claim 14 wherein the interior plane is curvilinear.

16. A sensor for monitoring oxygenation and adaptable for attaching to a patient, the sensor comprising:
a housing substantially surrounding an interior, the housing including an interior wall comprising a first material and having an outlet, the interior wall is capable of being placed proximate the patient;
an inset housing including a second material, the inset housing inlaid within the outlet;
a light source substantially surrounded by the inset housing wherein an exposed portion of the light source is positioned proximate the interior wall so as to project light produced by the light source toward the interior of the housing; and,
a light detector operatively attached to the housing and proximate the interior.

17. The sensor of claim 16 wherein the first material is substantially less reflective and/or transmissive to light than the second material.

18. The sensor of claim 16 further comprising:
an interior plane, wherein the light source and the light detector lie within a plane substantially coplanar with the interior plane.

19. The sensor of claim 16 wherein a portion of the interior wall is continuous.

20. A sensor utilized in monitoring patient oxygenation, the sensor comprising:
a housing including a first material being substantially non-reflective and/or non-transmissive to light, the housing including an interior and an interior surface, the interior surface including an opening;
an inset housing including a second material being substantially reflective, transmissive—or a combination thereof—to light, the inset housing inlaid within the opening of the interior surface; and,
a light source substantially surrounded by the inset housing wherein an exposed portion of the light source is proximate the interior surface so as to project light toward the interior of the housing.

21. The sensor of claim 20 wherein the inset housing intersects the interior surface and extends into the interior of the housing.

22. The sensor of claim 20 wherein the light source intersects the interior surface and extends into the interior of the housing.

23. The sensor of claim 22 wherein the inset housing intersects the interior surface and extends into the interior of the housing.

24. The sensor of claim 20 further comprising:
a transparent material positioned proximate the exposed portion of the light source.

25. The sensor of claim 24 wherein the transparent material is a pane coplanar with the interior surface.

26. The sensor of claim 20 wherein the first material comprises a dark color.

27. The sensor of claim 26 wherein the dark color is black or gray.

28. The sensor of claim 20 wherein the second material comprises a light color.

29. The sensor of claim 28 wherein the light color is white.

30. The sensor of claim 20 wherein the light source illuminates red wavelength.

31. The sensor of claim 20 wherein the light source illuminates infrared wavelength.

32. The sensor of claim 20 further comprising:
a detector for receiving illuminations from the light source, the detector being operatively attached to the interior surface of the housing.

33. The sensor of claim 20 wherein the housing comprises a flexible material.

34. The sensor of claim 20 wherein a portion of the interior surface is coplanar with an interior plane, and a portion of the first material and a portion of the second material are coplanar with the interior plane.

35. The sensor of claim 34 wherein the interior plane is curvilinear.

36. The sensor of claim 20 wherein a portion of the interior surface is coplanar with an interior plane, and a portion of the inset housing intersects the interior plane.

37. The sensor of claim 20 wherein a portion of the interior surface is continuous.

* * * * *